(12) United States Patent
Belloni

(10) Patent No.: US 6,794,416 B2
(45) Date of Patent: Sep. 21, 2004

(54) METHODS, COMPOSITIONS AND MODES OF DELIVERY FOR THE TREATMENT OF EMPHYSEMA USING 13-CIS-RETINOIC ACID

(75) Inventor: Paula N Belloni, Half Moon Bay, CA (US)

(73) Assignee: Syntex (U.S.A.) LLC, Palo Alto, CA (US)

(*) Notice: Subject to any disclaimer, the term of this patent is extended or adjusted under 35 U.S.C. 154(b) by 0 days.

(21) Appl. No.: 09/966,202

(22) Filed: Sep. 26, 2001

(65) Prior Publication Data

US 2002/0049252 A1 Apr. 25, 2002

Related U.S. Application Data

(62) Division of application No. 09/631,151, filed on Aug. 2, 2000, now Pat. No. 6,339,107.

(51) Int. Cl.$^7$ .............................................. A61K 31/07
(52) U.S. Cl. ........................................ 514/725; 424/45
(58) Field of Search ............................ 424/45; 514/725

(56) References Cited

U.S. PATENT DOCUMENTS

| 4,765,539 A | 8/1988 | Noakes et al. |
| 4,962,885 A | 10/1990 | Coffee |
| 5,112,598 A | 5/1992 | Biesalski |
| 5,556,611 A | 9/1996 | Biesalski |
| 5,698,593 A | 12/1997 | Peck |
| 5,950,619 A | 9/1999 | van der Linden et al. |
| 5,954,047 A | 9/1999 | Armer et al. |
| 5,970,974 A | 10/1999 | Van Der Linden et al. |
| 5,998,486 A | 12/1999 | Massaro et al. |
| 6,339,107 B1 * | 1/2002 | Belloni ........................ 514/725 |
| 6,515,022 B2 * | 2/2003 | Tong et al. .................. 514/559 |

FOREIGN PATENT DOCUMENTS

| DE | 0 579 915 A1 * | 5/1993 |
| EP | 0 579 915 A1 | 1/1994 |
| EP | 0597915 A | 12/1999 |
| WO | WO 94/12285 | 6/1994 |
| WO | WO 94/14543 | 7/1994 |
| WO | WO 95/26234 | 10/1995 |
| WO | WO 95/26235 | 10/1995 |
| WO | WO 95/32807 | 12/1995 |
| WO | WO 97/39745 | 10/1997 |
| WO | WO 99/47196 | 9/1999 |

OTHER PUBLICATIONS

Brazzell et al., 1983, "Pharmacokinetics of Isotretinoin During Repetitive Dosing to Patients," *Eur. J. Clin. Pharmacol.* 24:695–702.

Colburn et al., 1983, "Food Increases the Bioavailability of Isotretinoin," *J. Clin. Pharmacol.* 23:534–539.

Colburn et al., 1983, "Pharmacokinetics of Isotretinoin and Its Major Blood Metabolite Following a Single Oral Dose to Man," *Eur. J. Clin. Pharmacol.* 24:689–694.

Dahl et al., "Inhaled 13–cis Retinoic Acid is a Lung Cancer Chemopreventative in A/J Mice," Poster 527 at American Association of Cancer Research, San Francisco, CA, Apr. 1–5, 2000.

Engelke et al., "Pharmacokinetics of Inhaled 13–cis Retionic Acid (13–cis RA)," Poster 342 at American Association of Cancer Research, San Francisco, CA, Apr. 1–5, 2000.

Khoo et al., 1982, "Pharmacokinetics of Isotretinoin Following a Single Oral Dose," *J. Clin. Pharmacol.* 22:395–402.

Lucek and Colburn, 1985, "Clinical Pharmacokinetics of the Retinoids," *Clinical Pharmacokinetics* 10:38–62.

Massaro and Massaro, 1996, "Postnatal treatment with retinoic acid increases the number of pulmonary alveoli in rats," *Am. J. Physiol.* 270:L305–L310.

Massaro and Massaro, 1997, "Retinoic acid treatment abrogates elastase–induced pulmonary emphysema in rats," *Nature Med.* 3:675–677.

Raleigh et al., 1999, "Preclinical evaluation of an isotretinoin (iso) powder formulation for aerosol adminstration in lung cancer chemoprevention," *Proc. Amer. Assoc. Cancer Research Annual Meeting* 40:397, Abstract #2629.

Raleigh et al., 1999, "Pharmacokinetics of isotretinoin (iso) in rats following oral dosing or aerosol inhalation," *British Journal of Cancer* 80(Suppl 2):96, Abstract P269.

Toma et al., 1999, "Retinoids in lung cancer chemoprevention and treatment," *Annals of Oncology* 10(Suppl. 5):S95–S102.

Sklan, et al., "Inhibition of the Activity of Human Leukocyte Elastase by Lipids Particularly Oleic Acid and Retinoic Acid," *Lung*, (1990) pp 323–332, vol. 168:6 (XP–001051569).

* cited by examiner

Primary Examiner—Shelley A. Dodson
Assistant Examiner—Konata M. George
(74) Attorney, Agent, or Firm—Brian L. Buckwalter

(57) ABSTRACT

The current invention is directed to methods of treating or preventing emphysema, pharmaceutical compositions suitable for the treatment or prevention of emphysema and methods for delivering formulations into the lung of a mammal suffering from emphysema.

More generally, the invention encompasses the use of 13-cis-retinoic acid to treat or prevent certain chronic obstructive airway disorders, particularly chronic obstructive pulmonary disease including chronic bronchitis, emphysema and asthma in mammals, especially humans that smoke or smoked cigarettes. In another aspect, the present invention encompasses the use of pharmaceutical compositions of 13-cis-retinoic acid to treat emphysema. Moreover, the current invention encompasses the use of electrohydrodynamic aerosol devices, aerosol devices and nebulizers to deliver formulations of 13-cis-retinoic acid into the lung of a mammal suffering from emphysema. The invention also encompasses the systemic use as well as the local use of 13-cis-retinoic acid. In a another aspect the current invention encompasses a pharmaceutical composition for preventing emphysema in a human at risk of emphysema through administration of a amount of 13-cis-retinoic acid, or a pharmaceutically acceptable salt, hydrate, solvate, or prodrug thereof in a pharmaceutically acceptable carrier, that is sufficient to prevent emphysema.

33 Claims, No Drawings

METHODS, COMPOSITIONS AND MODES OF DELIVERY FOR THE TREATMENT OF EMPHYSEMA USING 13-CIS-RETINOIC ACID

This is a divisional of Ser. No. 09/631,151 filed Aug. 2, 2000, now U.S. Pat. No. 6,339,107.

1. FIELD OF THE INVENTION

The invention relates to methods of treating emphysema with 13-cis-retinoic acid, pharmaceutical compositions of 13-cis-retinoic acid useful in the treatment of emphysema and methods for delivering formulations of 13-cis-retinoic acid to the lung of a mammal suffering from emphysema.

2. BACKGROUND OF THE INVENTION

2.1. 13-Cis-Retinoic Acid

Chemically, 13-cis-retinoic acid is (13Z)-retinoic acid and has the following structure:

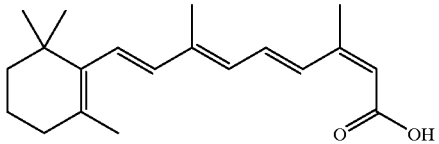

13-cis-retinoic acid is also known as isotretinoin, AGN 190013, Neovitamin A acid, Ro-4-3780, 13-cis-β-Retinoic acid and 13-cis-Vitamin A acid. 13-cis-retinoic acid is sold under the tradenames Accutane®, Roaccutan® and Roaccutane® for the treatment of severe recalcitrant nodular acne (*Physicians' Desk Reference* 54th Ed., p. 2610, 2000; Peck et al., *N. Eng. J. Med.*; Peck et al., U.S. Pat. No. 5,698,593). 13-cis-Retinoic acid has also been reported to be effective in treating psychotic illnesses such as schizophrenia (Straw, U.S. Pat. No. 4,808,630) and cancer of head, neck and lung (Tomas et al., *Annals of Oncology*, 1999, 10, 95; Benner et al., *Seminars in Hematology*, 1994, 31, 26). 13-cis-Retinoic acid is currently in clinical trials for treatment of these forms of cancer at a number of locations (e.g., University of Texas SW Medical Center, Dallas Tex.; University of Texas MD Anderson Cancer Center, Houston, Tex.; Department of Veteran Affairs Medical Center, Temple, Tex.).

13-cis-retinoic acid is a member of the retinoid class of compounds which are structural analogues of vitamin A and include both natural and synthetic compounds. Naturally occurring retinoid compounds such as all trans retinoic acid ("ATRA"), 9-cis-retinoic acid, trans 3-4 didehydroretinoic acid, 4-oxo retinoic acid and retinol are pleiotrophic regulatory compounds that influence a large number of inflammatory, immune and structural cells.

For example, retinoids modulate epithelial cell proliferation, morphogenesis in lung and differentiation through a series of nuclear receptors that belong to the steroid/thyroid receptor superfamily. In tissues other than pulmonary tissues, retinoids typically have anti-inflammatory effects, can alter the progression of epithelial cell differentiation and may inhibit stromal cell matrix production. These biological effects of retinoids have led to the development of many topical agents for dermatological disorders such as psoriasis, acne, and hypertrophic cutaneous scars. Other medicinal applications of retinoids include the control of acute promyelocytic leukemia, adeno and squamous cell carcinoma and hepatic fibrosis. However, retinoids often lack selectivity and consequently exert harmful pleiotrophic effects when used in therapeutically effective amounts, which may cause patient death. Thus, the therapeutic use of retinoids in diseases other then cancer has been limited by toxic side effects. A general review of retinoids can be found in Goodman & Gilman's "The Pharmacological Basis of Therapeutics", 9th edition (1996, McGraw-Hill) Chapters 63–64.

2.2. Emphysema

Chronic Obstructive Pulmonary Disease ("COPD") refers to a large group of lung diseases which prevent normal respiration. Approximately 11% of the population of the United States has COPD and available data suggests that the incidence of COPD is increasing. Currently, COPD is the fourth leading cause of mortality in the United States.

COPD is a disease in which the lungs are obstructed due to the presence of at least one disease selected from asthma, emphysema and chronic bronchitis. The term COPD was introduced because these conditions often co-exist and in individual cases it may be difficult to ascertain which disease is responsible for causing the lung obstruction (1987 *Merck Manual*). Clinically, COPD is diagnosed by reduced expiratory flow from the lungs that is constant over several months and in the case of chronic bronchitis persists for two or more consecutive years. The most severe manifestations of COPD typically include symptoms characteristic of emphysema.

Emphysema is a disease where the gas-exchange structures (e.g., alveoli) of the lung are destroyed, which causes inadequate oxygenation that may lead to disability and death. Anatomically, emphysema is defined by permanent airspace enlargement distal to terminal bronchioles (e.g., breathing tubes) which is characterized by reduced lung elasticity, decreased alveolar surface area and gas exchange and alveolar destruction that results in decreased respiration. Thus, the characteristic physiological abnormalities of emphysema are reduced gas exchange and expiratory gas flow.

Cigarette smoking is the most common cause of emphysema although other environmental toxins may also contribute to alveoli destruction. The injurious compounds present in these harmful agents can activate destructive processes that include, for example, the release of excessive amounts of proteases that overwhelm normal protective mechanisms, such as protease inhibitors present in the lung. The imbalance between proteases and protease inhibitors present in the lung may lead to elastin matrix destruction, elastic recoil loss, tissue damage, and continuous lung function decline. The rate of lung damage may be decreased by reducing the amounts of toxins in the lung (i.e., by quitting smoking). However, the damaged alveolar structures are not repaired and lung function is not regained. At least four different types of emphysema have been described according to their locations in the secondary lobule: panlobar emphysema, centrilobular emphysema, distal lobular emphysema and paracicatrical emphysema The major symptom of emphysema is chronic shortness of breath. Other important symptoms of emphysema include but are not limited to chronic cough, coloration of the skin caused by lack of oxygen, shortness of breath with minimal physical activity and wheezing. Additional symptoms that may be associated with emphysema include but are not limited to vision abnormalities, dizziness, temporary cessation of respiration, anxiety, swelling, fatigue, insomnia and memory loss. Emphysema is typically diagnosed by a physical examination that shows decreased and abnormal breathing sounds, wheezing and prolonged exhalation. Pulmonary function tests, reduced oxygen levels in the blood and a chest X-ray may be used to confirm a diagnosis of emphysema.

No effective methods for reversing the clinical indications of emphysema currently exist in the art. In some instances, medications such as bronchodilators, β-agonists, theophylline, anticholinergics, diuretics and corticosteroids delivered to the lung by an inhaler or nebulizer may improve respiration impaired by emphysema. Oxygen treatment is frequently used in situations where lung function has been so severely impaired that sufficient oxygen cannot be absorbed from the air. Lung reduction surgery may be used to treat patients with severe emphysema. Here, damaged portions of the lung are removed, which allows the normal portions of the lung to expand more fully and benefit from increased aeration. Finally, lung transplantation is another surgical alternative available to individuals with emphysema, which may increase quality of life but does not significantly improve life expectancy.

2.3. Lung Development, Alveolar Septation and Use of Atra in Treating Emphysema Alveoli are formed during development by division of sacchules that constitute the gas-exchange elements of the immature lung. The precise mechanisms governing formation of septa and their spacing remain currently unknown in primates. Retinoids such as ATRA, which is a multifunctional modulator of cellular behavior that may alter both extracellular matrix metabolism and normal epithelial differentiation, have a critical regulatory role in mammals such as the rat. For example, ATRA modulates critical aspects of lung differentiation through binding to specific retinoic acid receptors that are selectively temporally and spatially expressed. Coordinated activation of different retinoic acid receptors subtypes has been associated with lung branching, alveolization/septation and gene activation of tropoelastin in neonatal rats.

During alveolar septation, retinoic acid storage granules increase in the fibroblastic mesenchyme surrounding alveolar walls (Liu et al., *Am. J. Physiol.* 1993, 265, L430; McGowan et al., *Am. J. Physiol.,* 1995, 269, L463) and retinoic acid receptor expression in the lung peaks (Ong et al., *Proc. Natl. Acad. of Sci.,* 1976, 73, 3976; Grummer et al., *Pediatr. Pulm.* 1994, 17, 234). The deposition of new elastin matrix and septation parallels depletion of these retinoic acid storage granules. Postnatal administration of retinoic acid has been shown to increase the number of alveoli in rats, which supports the concept that ATRA may induces alveoli formation (Massaro et al., *Am. J. Physiol.,* 270, L305, 1996). Treatment of newborn rat pups with dexamethasone, a glucocorticosteroid, prevents septation and decreases expression of some sub-types of retinoic acid receptor. Supplemental amounts of ATRA have been shown to prevent dexamethasone inhibition of alveoli formation. Further, ATRA prevents dexamethasone from diminishing retinoic acid receptor expression and subsequent alveolar septation in developing rat lung.

ATRA has been reported to induce formation of new alveoli and returns elastic recoil in the lung to approximately normal values in animal models of emphysema (Massaro et al., *Nature Med.,* 1997, 3, 675; "Strategies to Augment Alveolization," National Heart, Lung, and Blood Institute, RFA: HL-98-011, 1998; Massaro et al., U.S. Pat. No. 5,998,486). However, the mechanism of action of ATRA in these studies remains undefined, although Massaro reports that ATRA generates new alveoli. More importantly, the use of ATRA presents several toxicity or adverse effects concerns. Thus, a drug useful for treating emphysema without the toxicity problems of ATRA would be highly desirable.

3. SUMMARY OF THE INVENTION

The current invention is directed to methods of treating or preventing emphysema, pharmaceutical compositions suitable for the treatment or prevention of emphysema and methods for delivering formulations into the lung of a mammal suffering from emphysema.

More generally, the invention encompasses the use of 13-cis-retinoic acid to treat or prevent certain chronic obstructive airway disorders, particularly chronic obstructive pulmonary disease including chronic bronchitis, emphysema and asthma in mammals, especially humans that smoke or smoked cigarettes. In a preferred embodiment, the invention encompasses the treatment or prevention of panlobar emphysema, centrilobular emphysema or distal lobular emphysema in mammals using non-toxic and therapeutically effective doses of 13-cis-retinoic acid.

In one embodiment, the present invention encompasses the use of 13-cis-retinoic acid for treating or preventing emphysema. Further, the instant invention encompasses the use of pharmaceutical compositions of 13-cis-retinoic acid to treat or prevent emphysema. Moreover, the current invention encompasses the use of electrohydrodynamic aerosol devices, aerosol devices and nebulizers to deliver formulations of 13-cis-retinoic acid into the lung of a mammal suffering from or at risk of emphysema.

The invention encompasses the systemic use as well as the local use of 13-cis-retinoic acid or both in combination. Either or both can be achieved by the oral, mucosal or parenteral modes of administration. As mentioned above, means of delivering 13-cis-retinoic acid directly into the lung by nebulizer, inhaler or other known delivery devices are encompassed by the invention.

A method for treating emphysema by combining 13-cis-retinoic acid with one or more additional therapies such as smoking cessation (where appropriate) bronchodilators, antibiotics, oxygen therapy and the like is also encompassed by the invention.

In another aspect, the current invention encompasses methods for preventing emphysema in a human at risk of emphysema through administration of an amount of 13-cis-retinoic acid, or a pharmaceutically acceptable salt, hydrate, solvate, or pro-drug thereof, that is sufficient to prevent emphysema. In a final aspect, the current invention encompasses pharmaceutical compositions for preventing emphysema in a human at risk of emphysema through administration of a amount of 13-cis-retinoic acid, or a pharmaceutically acceptable salt, hydrate, solvate, or pro-drug thereof in a pharmaceutically acceptable carrier, that is sufficient to prevent emphysema.

3.1 Definitions

As used herein, the term "mammal" includes human. The terms "human" and "patient" are used interchangeably herein.

As used herein, the term "treating emphysema" means alleviating, ameliorating, reducing, or relieving at least one symptom of emphysema. Symptoms of emphysema include, but are not limited to chronic cough, coloration of the skin caused by lack of oxygen, shortness of breath with minimal physical activity, wheezing, abnormal enlargement of the airspaces distal to the terminal bronchioles and destruction of their walls.

As used herein, the term "pharmaceutically acceptable salts" refers to salts prepared from pharmaceutically acceptable non-toxic organic or inorganic bases. Suitable organic bases include, but are not limited to, lysine, N,N'-dibenzylethylenediamine, chloroprocaine, choline, diethanolamine, ethylenediamine, meglumine (N-methylglucamine) and procaine. Suitable inorganic bases include, but are not limited to, alkaline and earth-alkaline metals such as aluminum, calcium, lithium, magnesium, potassium, sodium and zinc.

As used herein "pro-drug" refers to any compound which releases an active drug in vivo when such a compound is administered to a mammalian subject. Pro-drugs can be prepared, for example, by functional group modification of a parent drug. The functional group may be cleaved in vivo to release the active parent drug compound. Pro-drugs include, for example, compounds in which a group that may be cleaved in vivo is attached to a hydroxy, amino or carboxyl group in the active drug. Examples of pro-drugs include, but are not limited to esters (e.g., acetate, methyl, ethyl, formate, and benzoate derivatives), carbamates, amides and ethers. Methods for synthesizing such pro-drugs are known to those of skill in the art.

Reference will now be made in detail to preferred embodiments of the invention. While the invention will be described in conjunction with preferred embodiments, it should be understood that it is not intended to limit the invention to these preferred embodiments. To the contrary, it is intended to cover alternatives, modifications, and equivalents as may be included within the spirit and scope of the invention as defined by the appended claims.

4. DETAILED DESCRIPTION OF THE INVENTION

The invention is based, in part, upon the unexpected discovery that 13-cis-retinoic acid has a therapeutic profile substantially superior to that of its isomer ATRA when used to treat emphysema and related disorders (See, e.g., Example 6, below). Thus, invention described herein encompasses a safer and more efficacious emphysema therapy.

The present invention involves using 13-cis-retinoic acid to effectively treat emphysema. The invention encompasses treating emphysema and related disorders, while reducing or avoiding adverse effects associated with ATRA when used at therapeutic levels. Adverse effects associated with ATRA at therapeutic levels include, but are not limited to, the toxic effects of hypervitaminosis A, such as headache, fever, skin and membrane dryness, bone pain, nausea and vomiting, psychiatric disorders and gastrointestinal disorders.

A first aspect of the invention encompasses a method of treating emphysema in a mammal which comprises administering to a mammal in need of such treatment a therapeutically effective amount of 13-cis-retinoic acid, or a pharmaceutically acceptable salt, hydrate, solvate or pro-drug thereof. In one embodiment, the emphysema is panlobar emphysema, centrilobular emphysema or distal emphysema.

Preferably, the therapeutically effective amount of 13-cis-retinoic acid, or a pharmaceutically acceptable salt, hydrate, solvate, or pro-drug thereof, is between about 0.1 µg and about 10.0 mg, more preferably between about 1.0 µg and about 1.0 mg. In one embodiment, especially for oral administration, the therapeutically effective amount of 13-cis-retinoic acid, or pharmaceutically acceptable salt, hydrate, solvate, or pro-drug thereof is between about 100.0 µg and about 300.0 µg. In another embodiment, especially for administration by inhalation, the therapeutically effective amount of 13-cis-retinoic acid, or pharmaceutically acceptable salt, hydrate, solvate, or pro-drug thereof is between about 1.0 µg and about 100.0 µg, more preferably between about 3.0 µg and about 30.0 µg, most preferably between about 5.0 µg and about 15.0 µg.

This aspect of the invention encompasses a method of treating emphysema in a mammal by repairing alveoli in a mammal. In a preferred embodiment, the mammal is human. Preferably, the human was or is a cigarette smoker. In another preferred embodiment, a electrohydrodynamic aerosol device or a nebulizer device or a aerosol device is used to administer the therapeutically effective amount of 13-cis-retinoic acid, or pharmaceutically acceptable salt, hydrate, solvate, or pro-drug thereof.

A second aspect of the invention encompasses a pharmaceutical composition for the treatment of a mammal suffering from emphysema comprising an amount of 13-cis-retinoic acid, or a pharmaceutically acceptable salt, hydrate, solvate, or pro-drug thereof in a pharmaceutically acceptable carrier, with the amount of 13-cis-retinoic acid sufficient to alleviate one symptom of emphysema. In one embodiment, the emphysema is panlobar emphysema, centrilobular emphysema or distal emphysema. In a preferred embodiment, the mammal is human. Preferably, the human was or is a cigarette smoker.

The major symptoms of emphysema include but are not limited to chronic shortness of breath, chronic cough, coloration of the skin caused by lack of oxygen, shortness of breath with minimal physical activity and wheezing. Additional symptoms that may be associated with emphysema include, but are not limited to vision abnormalities, dizziness, temporary cessation of respiration, anxiety, swelling, fatigue, insomnia and memory loss.

Preferably, the amount of 13-cis-retinoic acid, pharmaceutically acceptable salt, hydrate, solvate, or pro-drug thereof, in the pharmaceutical composition, is between about 0.1 µg and about 10.0 mg, more preferably between about 1.0 µg and about 1.0 mg, most preferably between about 100.0 µg and about 300.0 µg.

In one embodiment, the pharmaceutically acceptable carrier is suitable for a electrohydrodynamic aerosol device, a nebulizer device or a aerosol device. In one preferred embodiment, the pharmaceutically acceptable carrier is a liquid such as water, alcohol, polyethylene glycol or perfluorocarbon. The amount of 13-cis-retinoic acid, or pharmaceutically acceptable salt, hydrate, solvate, or pro-drug thereof in the pharmaceutical composition in this preferred embodiment is between about 1.0 µg and about 100.0 µg, more preferably between about 3.0 µg and about 30.0 µg, most preferably between about 5.0 µg and about 15.0 µg.

A third aspect of the invention encompasses a method for treating emphysema and related disorders by delivering a formulation of 13-cis-retinoic acid or a pharmaceutically acceptable salt, hydrate, solvate, or pro-drug thereof into the lungs of a mammal. Preferably, the mammal is a human, more preferably, the human was or is a cigarette smoker. In one embodiment, the formulation is delivered into the lungs of the mammal with a nebulizer device. In a second embodiment, the formulation is delivered into the lungs of the mammal with a aerosol device. In a third embodiment, the formulation is delivered into the lungs of the mammal with a electrohydrodynamic aerosol device.

In an exemplary embodiment, the formulation is a pharmaceutical composition of 13-cis-retinoic acid. Preferably, the amount of 13-cis-retinoic acid, or pharmaceutically acceptable salt, hydrate, solvate, or pro-drug thereof in the pharmaceutical composition is between about 1.0 μg and about 100.0 μg, more preferably between about 3.0 μg and about 30.0 μg, most preferably between about 5.0 μg and about 15.0 μg. In one preferred embodiment, the pharmaceutically acceptable vehicle is a liquid such as water, alcohol, polyethylene glycol or perfluorocarbon. In another preferred embodiment, a material that alters the aerosol properties of the formulation is added to the formulation. Preferably, the material is an alcohol, glycol, polyglycol or fatty acid.

In a fourth aspect, the present invention encompasses a method for treating emphysema that combines use of 13-cis-retinoic acid with one or more additional therapies. The additional therapies include, but are not limited to, smoking cessation, antibiotics, bronchodilators and oxygen therapy. In a preferred embodiment, a pharmaceutical composition of 13-cis-retinoic acid is used in combination with other therapies.

In a fifth aspect, the current invention provides a method for preventing emphysema in a human at risk of emphysema by administering a amount of 13-cis-retinoic acid, or a pharmaceutically acceptable salt, hydrate, solvate, or pro-drug thereof sufficient to prevent emphysema. In a preferred embodiment, the human was or is a cigarette smoker.

In a final aspect the present invention provides a pharmaceutical composition that prevents emphysema in a human at risk of emphysema. The composition comprises an amount of 13-cis-retinoic acid or a pharmaceutically acceptable salt, hydrate, solvate, or pro-drug thereof and a pharmaceutically acceptable carrier that is sufficient to prevent emphysema.

4.1. Synthesis and Preparation

A number of methods for synthesizing 13-cis-retinoic acid have been described in the art. These include, but are not limited to, reaction of 4-hydroxy-3-methyl-butenolide and a Wittig salt followed by transition metal (i.e., Rh or Pd) catalyzed olefin isomerization (Lucci, U.S. Pat. No. 4,556, 518) and addition of a vinyl magnesium halide to provide vinyl-β-ionol, Witting condensation of vinyl-β-ionol with 4-hydroxy-3-methyl-butenolide and photochemical isomerization of the resulting alkali metal salts (Magnone et al., European Patent No. 959069). Other exemplary methods for 13-cis-retinoic acid synthesis include but are not limited to modified Wittig condensation of vinyl-β-ionol derivatives with 4-hydroxy-3-methyl-butenolide that provides the desired product stereospecifically, thus obviating the need for either transition metal or photochemical isomerization (Bhatia et al., PCT Application, WO 99/48866), oxidation of 13-cis-retinol with silver (I) oxide in the presence of base (Marbet, U.S. Pat. No. 3,746,730) and irradiation of 11-cis-retinoic acid with visible light in the presence of a photoactivator such as rose Bengal (Magnone, European Patent No. 742204). Other methods of making 13-cis-retinoic acid have been described in the art and will be known to the skilled artisan. 13-cis-retinoic acid is currently manufactured by Roche Pharmaceuticals (NJ).

4.2. Pharmaceutical Compositions and Modes of Administration

The methods of treatment using 13-cis-retinoic acid disclosed herein are useful for promoting the repair of damaged alveoli and septation of alveoli. Thus, these methods may be employed to treat pulmonary diseases such as emphysema.

When used to treat or prevent emphysema or related diseases 13-cis-retinoic acid may be administered or applied singly, in combination with other agents useful for treating emphysema or in combination with other pharmaceutically active agents. 13-cis-retinoic acid can be administered or applied per se or as pharmaceutical compositions. The specific pharmaceutical formulation will depend upon the desired mode of administration, and will be apparent to those having skill in the art. Numerous compositions for the topical or systemic administration of retinoids are known in the art. Any of these compositions may be formulated with 13-cis-retinoic acid.

Pharmaceutical compositions comprising 13-cis-retinoic acid may be manufactured by means of conventional mixing, dissolving, granulating, dragee-making, levigating, emulsifying, encapsulating, entrapping or lyophilizing processes. Pharmaceutical compositions may be formulated in conventional manner using one or more physiologically acceptable carriers, diluents, excipients or auxiliaries which facilitate processing of 13-cis-retinoic acid into preparations which can be used pharmaceutically. Proper formulation is dependent upon the route of administration chosen.

For topical administration 13-cis-retinoic acid may be formulated as solutions, gels, ointments, creams, suspensions, etc. as are well-known in the art.

Systemic formulations include those designed for administration by injection, e.g. subcutaneous, intravenous, intramuscular, intrathecal or intraperitoneal injection, as well as those designed for transdermal, transmucosal, oral or pulmonary administration. Systemic formulations may be made in combination with a further active agent that improves mucociliary clearance of airway mucus or reduces mucous viscosity. These active agents include but are not limited to sodium channel blockers, antibiotics, N-acetyl cysteine, homocysteine and phospholipids.

For injection, 13-cis-retinoic acid may be formulated in aqueous solutions, preferably in physiologically compatible buffers such as Hanks' solution, Ringer's solution, or physiological saline buffer. The solution may contain formulatory agents such as suspending, stabilizing and/or dispersing agents.

Alternatively, the 13-cis-retinoic acids may be in powder form for constitution with a suitable vehicle, e.g., sterile pyrogen-free water, before use.

For transmucosal administration, penetrants appropriate to the barrier to be permeated are used in the formulation. Such penetrants are generally known in the art.

For oral administration, 13-cis-retinoic acid can be readily formulated by combination with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. For oral solid formulations such as, for example, powders, capsules and tablets, suitable excipients include fillers such as sugars, such as lactose, sucrose, mannitol and sorbitol; cellulose preparations such as maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP); granulating agents and binding agents. If desired, disintegrating agents may be added, such as the cross-linked polyvinylpyrrolidone, agar, or alginic acid or a salt thereof such as sodium alginate. If desired, solid dosage forms may be sugar-coated or enteric-coated using standard techniques. Methods for formulating 13-cis-retinoic acid for oral administration are well known in the art (See, e.g the formulation of Accutane®, *Physicians' Desk Reference* 54$^{th}$ Ed., p. 2610, 2000).

For oral liquid preparations such as, for example, suspensions, elixirs and solutions, suitable carriers, excipients or diluents include water, saline, alkyleneglycols (e.g. propylene glycol), polyalkylene glycols (e.g. polyethylene glycol) oils, alcohols, slightly acidic buffers between pH 4 and pH 6 (e.g. acetate, citrate, ascorbate at between about 5.0 mM to about 50.0 mM) etc. Additionally, flavoring agents, preservatives, coloring agents, bile salts, acylcarnitines and the like may be added.

For buccal administration, the compositions may take the form of tablets, lozenges, etc. formulated in conventional manner.

13-cis-retinoic acid may also be administered directly to the lung by inhalation (see e.g., Tong et al., PCT Application, WO 97/39745; Clark et al., PCT Application, WO 99/47196, which are herein incorporated by reference). For administration by inhalation, 13-cis-retinoic acid may be conveniently delivered to the lung by a number of different devices. For example, a Metered Dose Inhaler ("MDI") which utilizes canisters that contain a suitable low boiling propellant, e.g., dichlorodifluoromethane, trichlorofluoromethane, dichlorotetrafluoroethane, carbon dioxide or other suitable gas may be used to deliver 13-cis-retinoic acid directly to the lung. MDI devices are available from a number of suppliers such as 3M Corporation, Aventis, Boehringer Ingleheim, Forest Laboratories, Glaxo-Wellcome, Schering Plough and Vectura.

Alternatively, a Dry Powder Inhaler (DPI) device may be used to administer 13-cis-retinoic acid to the lung (See, e.g,. Raleigh et al., *Proc. Amer. Assoc. Cancer Research Annual Meeting*, 1999, 40, 397, which is herein incorporated by reference). DPI devices typically use a mechanism such as a burst of gas to create a cloud of dry powder inside a container, which may then be inhaled by the patient. DPI devices are also well known in the art and may be purchased from a number of vendors which include, for example, Fisons, Glaxo-Wellcome, Inhale Therapeutic Systems, ML Laboratories, Qdose and Vectura. A popular variation is the multiple dose DPI ("MDDPI") system, which allows for the delivery of more than one therapeutic dose. MDDPI devices are available from companies such as AstraZeneca, GlaxoWellcome, IVAX, Schering Plough, SkyePharma and Vectura. For example, capsules and cartridges of gelatin for use in an inhaler or insufflator may be formulated containing a powder mix of the compound and a suitable powder base such as lactose or starch for these systems.

Another type of device that may be used to deliver 13-cis-retinoic acid to the lung is a liquid spray device supplied, for example, by Aradigm Corporation. Liquid spray systems use extremely small nozzle holes to aerosolize liquid drug formulations that may then be directly inhaled into the lung.

In a preferred embodiment, a nebulizer device is used to deliver 13-cis-retinoic acid to the lung. Nebulizers create aerosols from liquid drug formulations by using, for example, ultrasonic energy to form fine particles that may be readily inhaled (See e.g., Verschoyle et al., *British J. Cancer*, 1999, 80, Suppl 2, 96, which is herein incorporated by reference). Examples of nebulizers include devices supplied by Sheffield/Systemic Pulmonary Delivery Ltd. (See, Armer et al., U.S. Pat. No. 5,954,047; van der Linden et al., U.S. Pat. No. 5,950,619; van der Linden et a., U.S. Pat. No. 5,970,974, which are herein incorporated by reference), Aventis and Batelle Pulmonary Therapeutics. Inhaled 13-cis-retinoic acid, delivered by nebulizer devices, is currently under investigation as a treatment for aerodigestive cancer (Engelke et al., Poster 342 at American Association of Cancer Research, San Francisco, Calif., Apr. 1–5, 2000) and lung cancer (Dahl et a., Poster 524 at American Association of Cancer Research, San Francisco, Calif., Apr. 1–5, 2000).

In a particularly preferred embodiment, an electrohydrodynamic ("EHD") aerosol device is used to deliver 13-cis-retinoic acid to the lung. EHD aerosol devices use electrical energy to aerosolize liquid drug solutions or suspensions (see e.g., Noakes et al., U.S. Pat. No. 4,765,539; Coffee, U.S. Pat. No. 4,962,885; Coffee, PCT Application, WO 94/12285; Coffee, PCT Application, WO 94/14543; Coffee, PCT Application, WO 95/26234, Coffee, PCT Application, WO 95/26235, Coffee, PCT Application, WO 95/32807, which are herein incorporated by reference). The electrochemical properties of the 13-cis-retinoic acid formulation may be important parameters to optimize when delivering this drug to the lung with an EHD aerosol device and such optimization is routinely performed by one of skill in the art. EHD aerosol devices may more efficiently delivery drugs to the lung than existing pulmonary delivery technologies. Other methods of intra-pulmonary delivery of 13-cis-retinoic acid will be known to the skilled artisan and are within the scope of the invention.

Liquid drug formulations suitable for use with nebulizers and liquid spray devices and EHD aerosol devices will typically include 13-cis-retinoic acid with a pharmaceutically acceptable carrier. Preferably, the pharmaceutically acceptable carrier is a liquid such as alcohol, water, polyethylene glycol or a perfluorocarbon. Optionally, another material may be added to alter the aerosol properties of the solution or suspension of 13-cis-retinoic acid. Preferably, this material is liquid such as an alcohol, glycol, polyglycol or a fatty acid. Other methods of formulating liquid drug solutions or suspension suitable for use in aerosol devices are known to those of skill in the art (See, e.g., Biesalski, U.S. Pat. No. 5,112,598; Biesalski, U.S. Pat. No. 5,556,611, which are herein incorporated by reference)

13-cis-retinoic acid may also be formulated in rectal or vaginal compositions such as suppositories or retention enemas, e.g., containing conventional suppository bases such as cocoa butter or other glycerides.

In addition to the formulations described previously, 13-cis-retinoic acid may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Alternatively, other pharmaceutical delivery systems may be employed. Liposomes and emulsions are well known examples of delivery vehicles that may be used to deliver 13-cis-retinoic acid. Certain organic solvents such as dimethylsulfoxide also may be employed, although usually at the cost of greater toxicity. 13-cis-retinoic acid may also be delivered in a controlled release system. In one embodiment, a pump may be used (Sefton, *CRC Crit. Ref Biomed. Eng.*, 1987, 14, 201; Buchwald et al., *Surgery*, 1980, 88, 507;

Saudek et al., *N. Engl. J. Med.,* 1989, 321, 574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, N.Y. (1984); Ranger and Peppas, *J. Macromol. Sci. Rev. Macromol. Chem.,* 1983, 23, 61; see also Levy et al., *Science* 1985, 228, 190; During et al., *Ann. Neurol.,* 1989, 25, 351; Howard et al., 1989, *J. Neurosurg.* 71, 105). In yet another embodiment, a controlled-release system can be placed in proximity of the target of the compounds of the invention, e.g., the lung, thus requiring only a fraction of the systemic dose (see, e.g., Goodson, in Medical Applications of Controlled Release, supra, vol. 2, pp. 115 (1984)). Other controlled-release system may be used (see e.g. Langer, *Science,* 1990, 249, 1527).

As 13-cis-retinoic acid is acidic, it may be included in any of the above-described formulations as the free acid, a pharmaceutically acceptable salt, a pro-drug, solvate or hydrate. Pharmaceutically acceptable salts substantially retain the activity of the free acid and may be prepared by reaction with bases. Pharmaceutically acceptable salts include any known suitable salts of retinoic acids known in the art for administration to mammals. Pharmaceutical salts tend to be more soluble in aqueous and other protic solvents than is the corresponding free acid form. Similarly, the 13-cis-retinoic acids may be included in any of the above-described formulations as a solvate, hydrate or pro-drug. Preferred pro-drugs include hydrolyzable ester derivatives such as aromatic esters, benzyl esters and lower alkyl esters such as ethyl, cyclopentyl etc. Other pro-drugs are known to those of skill in the pharmaceutical arts.

4.3 Methods of Use, Dosage and Doses 13-cis-retinoic acid of the invention, or compositions thereof, will generally be used in an amount effective to achieve the intended purpose. Of course, it is to be understood that the amount used will depend on the method of administration.

For use to treat or prevent emphysema, 13-cis-retinoic acid or compositions thereof, are administered or applied in a therapeutically effective amount. By therapeutically effective amount is meant an amount effective to ameliorate the symptoms of, or ameliorate, treat or prevent emphysema. Therapeutically effective amounts of 13-cis-retinoic acid for systemic administration may be found in the detailed disclosure provided herein.

The pharmacokinetic profile of 13-cis-retinoic acid is predictable and can be described by using linear pharmacokinetic theory. Importantly, the pharmacokinetics of 13-cis-retinoic acid in humans is particularly well defined. A range of standard pharmacokinetic parameters after single oral dosing with 13-cis-retinoic acid has been described in the art (See e.g., Khoo et al., *J. Clin. Pharm,* 1982, 22, 395; Colburn et al., *J. Clin. Pharm,* 1983, 23, 534; Colburn et al., *Eur. J. Clin. Pharm.,* 1983, 23, 689). Similar values of pharmacokinetic parameters are found after multiple dosing, which indicates that induction or accumulation of 13-cis-retinoic acid does not occur under these circumstances (Brazzel et al., *Eur. J. Clin. Pharm.,* 1983, 24, 695; Lucek et al., *Clin. Pharmacokinetics,* 1985, 10, 38). Those of skill in the art may estimate the appropriate systemic dosage levels of 13-cis-retinoic acid necessary to treat emphysema in mammals (preferably, humans) using known pharmacokinetic parameters in conjunction with animal model dosage data.

Dosage amounts and intervals may be adjusted individually to provide plasma levels of 13-cis-retinoic acid which are sufficient to maintain therapeutic effect. Usual patient dosages for administration by injection range from 0.1 μg and about 10.0 mg, preferably, between about 1.0 μg and about 1.0 mg, more preferably, between about 100.0 μg and about 300.0 μg. Therapeutically effective serum levels may be achieved by administering a single daily dose or multiple doses each day.

The amount of 13-cis-retinoic acid administered will, of course, be dependent on, among other factors, the subject being treated, the subject's weight, the severity of the affliction, the manner of administration and the judgment of the prescribing physician. Typically, the oral dosage range will vary between 0.1 μg and about 10.0 mg, preferably, between about 1.0 μg and about 1.0 mg, more preferably, between about 100.0 μg and about 300.0 μg. Administration of 13-cis-retinoic acid formulations into the lung with a pulmonary drug delivery device may reduce the dose required between about 10 and about 100 fold. Thus, typically, the aerosol dosage range will vary between 1.0 μg and about 100.0 μg, preferably, between about 3.0 μg and about 30 μg, more preferably, between about 5 μg and about 15 μg. For example, the dosage may be delivered in a pharmaceutical composition by a single administration, by multiple applications or controlled release. Dosing may be repeated intermittently, may be provided alone or in combination with other drugs and will continue as long as required for effective treatment of emphysema.

Preferably, a therapeutically effective dose of 13-cis-retinoic acid described herein will provide therapeutic benefit without causing substantial toxicity. Toxicity of 13-cis-retinoic acid has been determined using standard pharmaceutical procedures and may be readily ascertained by the skilled artisan. The dose ratio between toxic and therapeutic effect is the therapeutic index. 13-cis-retinoic acid exhibits particularly high therapeutic indices in treating emphysema when compared to ATRA as demonstrated in Example 6. The dosage of the 13-cis-retinoic acids described herein lies within a range of circulating concentrations that include the effective dose with little or no toxicity. The dosage may vary within this range depending upon the dosage form employed and the route of administration utilized. The exact formulation, route of administration and dosage can be chosen by the individual physician in view of the patient's condition (See, e.g., Fingl et al., 1975, *In: The Pharmacological Basis of Therapeutics,* Ch. 1, p. 1). For example, a therapeutically effective dose of 13-cis-retinoic acid may be administered either orally or directly into the lung.

The invention is further defined by reference to the following examples describing in detail the preparation of the compound and compositions of the invention. It will be apparent to those skilled in the art that many modifications, both to materials and methods, may be practiced without departing from the scope of the invention.

5. EXAMPLES

5.1. Example 1

Oral Formulation of 13-Cis-Retinoic Acid

Table 1 provides the ingredients for a tablet dosage form of 13-cis-retinoic acid:

TABLE 1

| Component | Quantity per Tablet (mg) |
| --- | --- |
| 13-cis-retinoic acid | 0.1–10.0 |
| Lactose | 125.0 |

TABLE 1-continued

| Component | Quantity per Tablet (mg) |
|---|---|
| Corn Starch | 50 |
| Magnesium Stearate | 0.5 |
| Croscarmellose Sodium | 25 |

The active ingredient (i e., 13-cis-retinoic acid) is blended with the lactose until a uniform mixture is formed. The remaining ingredients are mixed intimately with the lactose mixture and are then pressed into single scored tablets.

5.2. Example 2

Oral Formulation of 13-Cis-Retinoic Acid

Capsules of 13-cis-retinoic acid suitable for the treatment of emphysema may be made using the ingredients provided in Table 2:

TABLE 2

| Component | Quantity per capsule (mg) |
|---|---|
| 13-cis-retinoic acid | 0.1–5.0 |
| Lactose | 148 |
| Magnesium Stearate | 2 |

The above ingredients are mixed intimately and loaded into a hard-shell gelatin capsule.

5.3. Example 3

Inhalation Formulation of 13-Cis-Retinoic Acid

TABLE 3

| Component | Percentage by weight |
|---|---|
| 13-cis-retinoic acid (stabilized with α-tocopherol) | 1.0 |
| 1,1,2-tricholoro-trifluoroethane | 26.1 |
| 40% by weight dichlorodifluoromethane and 60% by weight 1,2-dichloro-1,1,2,2 tetraflouroethane | 72.0 |

13-cis-retinoic acid is dissolved carefully in 1,1,2-tricholoro-1,2,2 trifluoroethane without evaporation of any solvent and the resultant solution is filtered and stored in a sealed container. The resultant solution and the propellant gas may be introduced into aerosol cans for dispensation in the percentages shown in Table 3 using methods known to the skilled artisan. A metering valve which is designed for a discharge of between 100 μg and 300 μg per spray shot may be employed to deliver the correct dosage of 13-cis-retinoic acid.

5.4. Example 4

Inhalation Formulation of 13-Cis-Retinoic Acid

TABLE 4

| Component | Percentage by weight |
|---|---|
| 13-cis-retinoic acid (stabilized with α-tocopherol) | 0.5 |
| Emulsifier (i.e., Cremophor RH 40) | 22.0 |

TABLE 4-continued

| Component | Percentage by weight |
|---|---|
| 1,2 propylene glycol | 2.0 |
| Water and carrier gas | ad 100% by weight |

Cremaphor RH 40 may be purchased from BASF corporation. Other emulsifiers or solutizers are known to those of skill in the art and may be added to the aqueous solvent instead of Cremaphor RH 40. 13-cis-retinoic acid, emulsifier, 1,2 propylene glycol and water are mixed together to form a solution. The above liquid formulation may be used, for example, in a pressurized gas aerosol with an appropriate carrier gas (e.g., nitrogen or carbon dioxide).

5.5. Example 5

EHD Formulation of 13-Cis-Retinoic Acid

TABLE 5

| Component | Percentage by weight |
|---|---|
| 13-cis-retinoic acid (stabilized with α-tocopherol) | 0.1 |
| Emulsifier (i.e., Cremophor RH 40) | 10.0 |
| Polyethylene glycol | 3.0 |
| Water | 86.9 |

13-cis-retinoic acid, emulsifier, polyethylene glycol and water are mixed together to form a solution. The above liquid formulation may be used in typical EHD devices known in the art.

5.6. Example 6

Comparison of ATRA and 13-Cis-Retinoic Acid in Rat Lung

All-trans retinoic acid (ATRA) and 13-cis-retinoic acid were evaluated for their effects on alveolar repair in the rat model of elastase-induced emphysema (Massaro et al., Nature, 1997, Vol. 3, No. 6:675; Massaro et al., U.S. Pat. No. 5,998,486). Animals were divided into treatment groups of approximately eight. Lung inflammation and alveolar damage was induced in male Sprague Dawley rats by a single instillation of about 2 U/gram body mass of pancreatic elastase (porcine derived, Calbiochem).

Animals treated with ATRA and 13-cis-retinoic acid prepared in Capmul at the dosage ranges enumerated in Table 6 were dosed orally once per day starting 21 days post injury. Control groups were challenged with elastase and 21 days later were treated with vehicle (Capmul solution) for 14 days. Animals were sacrificed 24 hours after the last dose by exsanguination under deep anesthesia. Blood was collected at time of exsanguination for analysis.

The lungs were inflated with 10% neutral buffered formalin by intratracheal instillation at a constant rate (1 ml/gram body mass/min). The lung was excised and immersed in fixative for 24 hours prior to processing. Alveolar measurements were made in four regions of the lung/rat. The mean value/treatment group was determined by summing the average area/rat for all eight rats relative to the elastase+ vehicle treated group. In some cases, the variability between rats within a treatment group was too large for the group average to be statistically significant. Standard methods were used to prepare 5 μm paraffin sections. Sections were stained with Hematoxylin and Eosin.

Computerized Morphometric analysis was performed to determine the average alveolar size and alveolar number.

Quantitation of triglycerides contained in rat plasma was performed using established procedures in a contact clinical laboratory facility. Briefly, plasma triglycerides were converted to dihdroxyacetone and hydrogen peroxide by sequential treatment of plasma with lipase and glycerokinase according directions described by the manufacturer of triglycerides/GPO kit (Boehringer Mannheim #1488872). Hydrogen peroxide was quantitated colorimetrically in a Hitachi 911 Chemistry Analyzer. In rats normal triglyceride levels are between about 75 mg/dl and about 175 mg/dl.

TABLE 6

| Active Component | Oral Dose (mg/kg) | % Alveolar Repair | Triglyceride (mg/dl) |
|---|---|---|---|
| ATRA | 10.0 | 53 | 378 |
| ATRA | 3.0 | 47 | 307 |
| ATRA | 1.0 | 45 | 175 |
| ATRA | 0.3 | 30* | 149 |
| ATRA | 0.1 | 8.8* | 152 |
| 13-cis-retinoic acid | 10.0 | 56 | 147 |
| 13-cis-retinoic acid | 1.0 | 45 | 128 |
| 13-cis-retinoic acid | 0.1 | 30 | 82 |
| 13-cis-retinoic acid | 0.01 | 38 | 73 |
| 13-cis-retinoic acid | 0.001 | 12* | 125 |

*Not statistically significant relative to elastase + vehicle control.

The results are shown above in Table 6. Triglyceride values are a convenient measure of toxicity. ATRA generally has triglyceride values that are above the normal range at dosage levels between 10 mg/kg and 1 mg/kg. At lower dosage ranges of 0.3 mg/kg and 0.1 mg/kg the triglyceride value of ATRA are within the acceptable range. By contrast, 13-cis-retinoic acid at both the high (10.0 mg/kg) and low (0.001 mg/kg) range exhibits triglyceride values that are well within the normal range. Thus, for every dosage of 13-cis retinoic acid, triglyceride levels are within the normal range, whereas triglyceride levels for ATRA are within the normal range only at low dosages. Furthermore, at every dosage level tested, the triglyceride levels observed with 13-cis-retinoic acid were lower than that observed for ATRA.

The results shown in Table 6 demonstrate that both ATRA and 13-cis-retinoic acid induce substantial alveolar repair at high dosage (e.g., between 10.0 mg/kg and 1.0 mg/kg). However, at dosages below 0.3 mg/kg the amount of alveolar repair effected by ATRA is not statistically significant relative to the elastase treated control group. In contrast, 13-cis-retinoic acid effects statistically significant alveoli repair at dosage range from 10.0 mg/kg to as low as 0.01 mg/kg. Only at a dosage of 0.001 mg/kg does the amount of alveolar repair effected by 13-cis-retinoic acid become statistically insignificant. Hence, ATRA is substantially less effective than 13-cis-retinoic acid in repairing alveoli at low dosages. Thus, although the efficacy of ATRA and 13-cis-retinoic acid are similar at high dosages, 13-cis-retinoic acid is considerably safer than ATRA, because unlike ATRA, it does not elevate triglycerides even at high dosages and it also efficacious at low dosages at which ATRA is ineffective. Thus, the therapeutic index of 13-cis-retinoic acid for treating emphysema is surprisingly more favorable when compared to the therapeutic index for treating ATRA. Finally, the data also show that ATRA, unlike 13-cis retinoic acid, does not have a statistically significant therapeutic effect at dosage levels where it does not elevate triglyceride levels above the normal range.

The embodiments of the invention described above are intended to be merely exemplary, and those skilled in the art will recognize, or be able to ascertain using no more than routine experimentation, numerous equivalents to the specific procedures described herein. All such equivalents are considered to be within the scope of the invention and are encompassed by the following claims.

What is claimed is:

1. A method of treating emphysema in a mammal comprising administering to a mammal in need of such treatment a therapeutically effective amount of 13-cis-retinoic acid, or a pharmaceutically acceptable salt, hydrate, solvate, or pro-drug thereof.

2. The method of claim 1, wherein the therapeutically effective amount of 13-cis-retinoic acid, or a pharmaceutically acceptable salt, hydrate, solvate, or pro-drug thereof, repairs alveoli in the mammal.

3. The method of claim 1, wherein the mammal is human.

4. The method of claim 3, wherein the human was or is a cigarette smoker.

5. The method of claim 1, wherein the emphysema is panlobar emphysema, centrilobular emphysema or distal lobular emphysema.

6. The method of claim 5, wherein the mammal is human.

7. The method of claim 6, wherein the human was or is a cigarette smoker.

8. The method of claim 1, wherein the therapeutically effective amount of 13-cis-retinoic acid, or a pharmaceutically acceptable salt, hydrate, solvate, or pro-drug thereof, is administered with an electrohydrodynamic aerosol device.

9. A pharmaceutical composition suitable for treating a mammal suffering from emphysema comprising an amount of 13-cis-retinoic acid or a pharmaceutically acceptable salt, hydrate, solvate, or pro-drug thereof, and a pharmaceutically acceptable carrier, said amount being sufficient to alleviate one symptom of emphysema.

10. The method of claim 9, wherein the emphysema is panlobar emphysema, centrilobular emphysema or distal lobular emphysema.

11. A pharmaceutical composition according in claim 9, wherein the pharmaceutical Composition is suitable far administration to the lungs by inhalation.

12. The pharmaceutical composition of claim 11, wherein the pharmaceutically acceptable carrier is suitable for electrohydrodynamic aerosol device, a aerosol device or a nebulizer device.

13. The pharmaceutical composition of claim 12, wherein the pharmaceutically acceptable carrier is a liquid.

14. The pharmaceutical composition of claim 13, wherein the pharmaceutically acceptable carrier is chosen from the group consisting of water, alcohol and perfluorocarbon.

15. The pharmaceutical composition of claim 13, wherein the amount of 13-cis-retinoic acid, or a pharmaceutically acceptable salt, hydrate, solvate, or pro-drug thereof, is between about 1.0 µg and about 100.0 µg.

16. The pharmaceutical composition of claim 15, wherein the amount of 13-cis-retinoic acid, or a pharmaceutically acceptable salt, hydrate, solvate, or pro-drug thereof, is between about 3.0 µg and about 30.0 µg.

17. The pharmaceutical composition of claim 16, wherein the amount of 13-cis-retinoic acid, or a pharmaceutically acceptable salt, hydrate, solvate, or pro-drug thereof, is between about 5.0 µg and about 15.0 µg.

18. The pharmaceutical composition of claim 11, wherein the amount of 13-cis-retionic acid, or a pharmaceutically acceptable salt, hydrate, solvate, or pro-drug thereof, is between about 0.1 µg and about 10.0 mg.

19. The pharmaceutical composition of claim 18, wherein the amount of 13-cis-retinoic acid, or a pharmaceutically acceptable salt, hydrate, solvate, or pro-drug thereof, is between about 1.0 µg and about 1.0 mg.

20. The pharmaceutical composition of claim 19, wherein the amount of 13-cis-retinoic acid, or a pharmaceutically acceptable salt, hydrate, solvate, or pro-drug thereof, is between about 100.0 µg and about 300.0 µg.

21. The pharmaceutical composition of claim 11, wherein said form is suitable for administration through a dry powder inhaler.

22. The pharmaceutical composition of claim 11, wherein said form is suitable for administration through a liquid spray device.

23. The pharmaceutical composition of claim 22, wherein said liquid spray device is an aerosol device.

24. The pharmaceutical composition of claim 23, wherein said aerosol device is a nebulizer or electrohydrodynamic aerosol device.

25. A method for treating emphysema and related disorders comprising delivering a formulation of 13-cis-retinoic acid, or a pharmaceutically acceptable salt, hydrate, solvate, or pro-drug thereof, into the lungs of a mammal.

26. The method of claim 25, wherein the emphysema is panlobar emphysema, centrilobular emphysema or distal lobular emphysema.

27. The method of claim 26, wherein the mammal is human.

28. The method of claim 27, wherein the human was or is a cigarette smoker.

29. The method of claim 25, wherein the formulation is delivered into the lungs of the mammal with a nebulizer device.

30. The method for treating emphysema and related disorders comprising delivering a formulation of 13-cis-retinoic acid, or a pharmaceutically aceptable salt, hydrate, solvate, or pro-drug thereof, into the lungs of the mammal with an aerosol device.

31. The method of claim 30, wherein the formulation is delivered into the lungs of the mammal with an electrohydrodynamic aerosol device.

32. A method for treating emphysema comprising combining the use of 13-cis-retinoic acid with one or more additional therapies.

33. The method of claim 32, wherein the additional therapies are chosen from the group consisting of smoking cessation, bronchodilators, antibiotics and oxygen therapy.

* * * * *